United States Patent
Maayan et al.

(10) Patent No.: US 11,027,236 B2
(45) Date of Patent: Jun. 8, 2021

(54) AIR TREATMENT SYSTEMS AND METHODS

(71) Applicants: AIROVATION TECHNOLOGIES LTD., Tel Aviv (IL); Yissum Research Development Company of the Hebrew University of Jerusalem Ltd., Jerusalem (IL)

(72) Inventors: Marat Maayan, Tel Aviv (IL); Uri Stoin, Jerusalem (IL); Yoel Sasson, Jerusalem (IL); Doron Weinfeld, Jerusalem (IL)

(73) Assignees: Airovation Technologies Ltd., Ness Ziona (IL); Yissum Research Development Company of the Hebrew University of Jerusalem Ltd., Jersualem (IL)

(*) Notice: Subject to any disclaimer, the term of this patent is extended or adjusted under 35 U.S.C. 154(b) by 280 days.

(21) Appl. No.: 16/311,005

(22) PCT Filed: Jun. 28, 2017

(86) PCT No.: PCT/IB2017/000925
§ 371 (c)(1),
(2) Date: Dec. 18, 2018

(87) PCT Pub. No.: WO2018/002710
PCT Pub. Date: Jan. 4, 2018

(65) Prior Publication Data
US 2020/0171431 A1 Jun. 4, 2020

Related U.S. Application Data

(60) Provisional application No. 62/355,375, filed on Jun. 28, 2016, provisional application No. 62/439,511, filed on Dec. 28, 2016.

(51) Int. Cl.
*B01D 53/78* (2006.01)
*B01D 53/30* (2006.01)
(Continued)

(52) U.S. Cl.
CPC ......... *B01D 53/78* (2013.01); *A61M 16/0488* (2013.01); *A61M 16/06* (2013.01);
(Continued)

(58) Field of Classification Search
CPC .......... Y02C 20/40; A61M 2202/0233; A61M 16/0488; A61M 16/06; F24F 2003/1628;
(Continued)

(56) References Cited

U.S. PATENT DOCUMENTS

| 6,398,971 B1 | 6/2002 | Butters et al. | |
| 2003/0056648 A1* | 3/2003 | Fornai | F24F 3/1603 95/65 |

(Continued)

FOREIGN PATENT DOCUMENTS

| AU | 2008 325164 A1 * | 5/2009 | ............. A62C 35/11 |
| CN | 1309261 A | 8/2001 | |

(Continued)

OTHER PUBLICATIONS

Written Opinion received from Intellectual Property Office of Singapore for Singapore Application No. 11201811034P, dated Jan. 3, 2020, 7 pages.

(Continued)

*Primary Examiner* — Timothy C Vanoy
(74) *Attorney, Agent, or Firm* — Finnegan, Henderson, Farabow, Garrett & Dunner, LLP

(57) ABSTRACT

An air treatment unit may include an air inlet to receive a flow of input air for treatment and a reaction reservoir configured to hold an aqueous air treatment solution. The air treatment unit may also include an air dispersing element (Continued)

Figure 1:
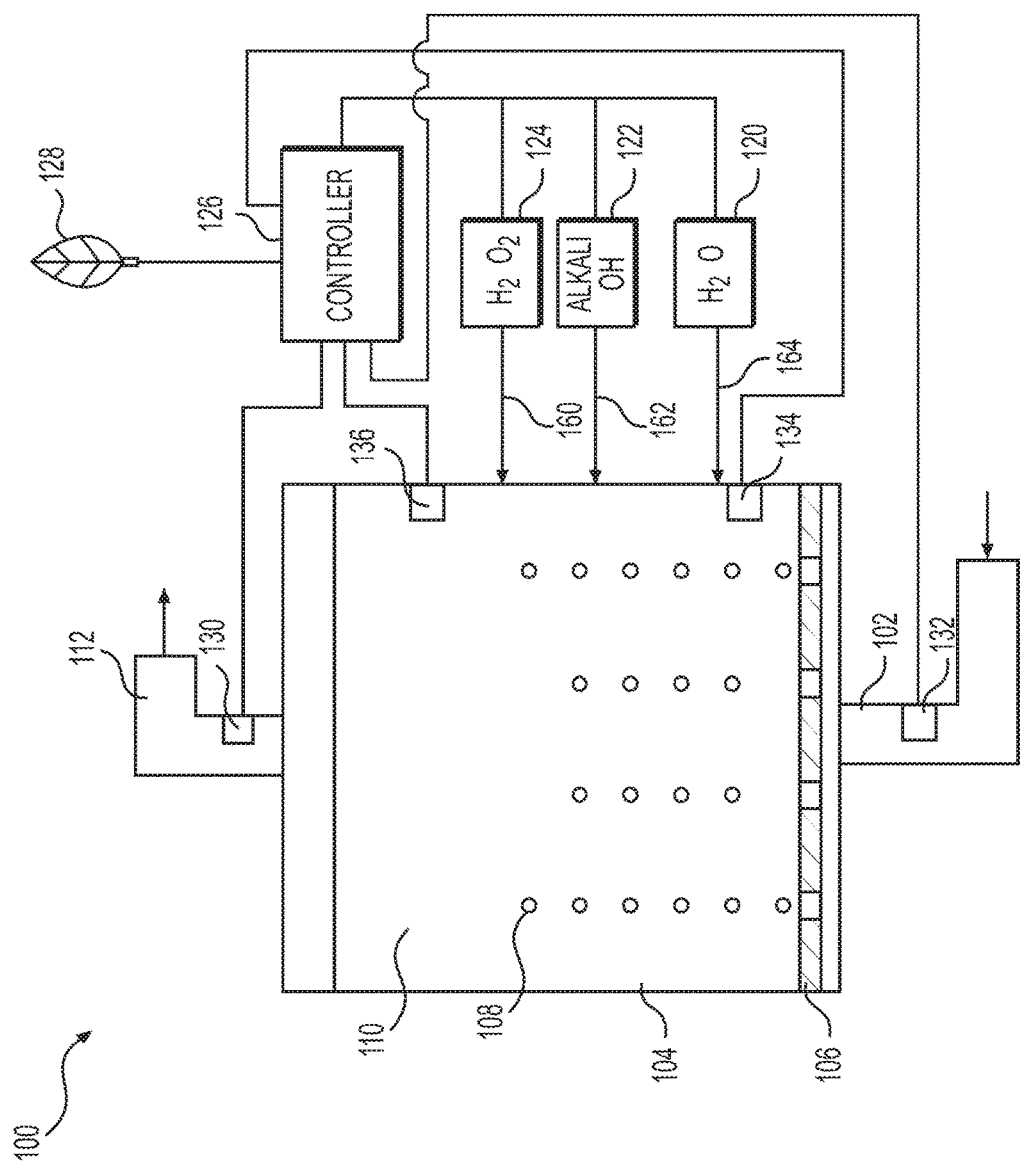

flow connected with the air inlet, wherein the air dispersing element is configured to convert at least a portion of the flow of input air into a plurality of microbubbles for introduction into the aqueous air treatment solution, such that an amount of one or more target gas species contained within the plurality of microbubbles is reduced through reaction with the aqueous air treatment solution. The unit may include an air outlet configured to output treated air from the reaction reservoir.

59 Claims, 9 Drawing Sheets

(51) Int. Cl.

| | | |
|---|---|---|
| *B01D 53/60* | (2006.01) | |
| *B01D 53/62* | (2006.01) | |
| *B01D 53/56* | (2006.01) | |
| *A61M 16/04* | (2006.01) | |
| *A61M 16/06* | (2006.01) | |
| *A61M 16/10* | (2006.01) | |
| *A62B 7/10* | (2006.01) | |
| *B66B 11/02* | (2006.01) | |
| *B01D 53/68* | (2006.01) | |
| *B01D 53/86* | (2006.01) | |

(52) U.S. Cl.
CPC ............. *A61M 16/105* (2013.01); *A62B 7/10* (2013.01); *B01D 53/30* (2013.01); *B01D 53/56* (2013.01); *B01D 53/60* (2013.01); *B01D 53/62* (2013.01); *B01D 53/68* (2013.01); *B01D 53/8653* (2013.01); *B66B 11/024* (2013.01); *A61M 2202/0233* (2013.01); *B01D 2251/106* (2013.01); *B01D 2251/302* (2013.01); *B01D 2251/304* (2013.01); *B01D 2251/306* (2013.01); *B01D 2251/404* (2013.01); *B01D 2251/604* (2013.01); *B01D 2257/2045* (2013.01); *B01D 2257/302* (2013.01); *B01D 2257/404* (2013.01); *B01D 2257/502* (2013.01); *B01D 2257/702* (2013.01); *B01D 2258/06* (2013.01)

(58) Field of Classification Search
CPC ....... F24F 2110/50; F24F 3/1603; A62B 7/10; A61L 9/00; A61L 9/14; A61L 9/145; A61L 2101/02; A61L 2202/25; A61L 2209/134; A61L 2209/21; A61L 2209/22
See application file for complete search history.

(56) References Cited

U.S. PATENT DOCUMENTS

| | | |
|---|---|---|
| 2005/0145108 A1 | 7/2005 | Rubin et al. |
| 2007/0267334 A1 | 11/2007 | Osborn et al. |
| 2008/0271603 A1* | 11/2008 | Triplett ................ B01D 53/025 95/150 |
| 2010/0104492 A1 | 4/2010 | May |
| 2012/0234740 A1 | 9/2012 | Drewelow |
| 2013/0042756 A1* | 2/2013 | Oda .......................... B03C 3/47 95/64 |
| 2013/0260462 A1 | 10/2013 | Wood et al. |

FOREIGN PATENT DOCUMENTS

| | | | | |
|---|---|---|---|---|
| CN | 1719092 A | | 1/2006 | |
| CN | 1899978 A | | 1/2007 | |
| CN | 101972591 A | | 2/2011 | |
| CN | 102307599 A | * | 1/2012 | ........ B05B 17/0669 |
| CN | 104203437 A | | 12/2014 | |
| DE | 2722013 A1 | | 11/1978 | |
| JP | S 4817713 B1 | | 5/1973 | |
| JP | 2005087429 A | | 4/2005 | |
| JP | 2008104907 A | | 5/2008 | |
| JP | 2010-75834 A | | 4/2010 | |
| JP | 2020-104988 A | | 5/2010 | |
| JP | 20061247070 A | | 5/2018 | |
| KR | 1999165 B1 | * | 7/2019 | ............. A61L 9/145 |
| KR | 2019 103603 A | * | 9/2019 | ............. A61L 9/145 |
| WO | WO 2013/093903 A1 | | 6/2013 | |
| WO | WO 2017 048034 A1 | * | 3/2017 | ............. A61L 9/145 |

OTHER PUBLICATIONS

Notice of Reasons for Rejection received from Japanese Patent Office Action for Japanese Application No. 2018-568860, dated Jan. 14, 2020, 11 pages.
International Search Report and Written Opinion for International Application No. PCT/IB2017/000925, dated Jun. 28, 2017 (16 pages).
Supplementary Partial European Search Report for European Application No. 17819427.0, dated Nov. 7, 2019 (15 pages).
Examination Report for Indian Patent Application No. 201847046000 and English translation thereof, dated Oct. 29, 2020 (6 pages).
Office Action for Japanese Patent Application No. 2018-568860 and English translation thereof, dated Nov. 10, 2020 (10 pages).
Notice of Allowance for Korean Patent Application No. 10-2019-7002609 and English translation thereof, dated Nov. 12, 2020 (3 pages).
Office Action for Canadian Patent Application No. 3,026,747, dated Dec. 30, 2020 (4 pages).
Extended European Search Report for European Application No. 17819427.0, dated Mar. 6, 2020 (12 pages).
Intention to Grant for European Application No. 17819427.0, dated Dec. 4, 2020 (39 pages).
First Office Action issued by National Intellectual Property Administration of the P.R. China (CNIPA) for Chinese Patent Application No. 2017800409301 and translation thereof, dated Mar. 1, 2021 (15 pages).

* cited by examiner

AIR TREATMENT SYSTEMS AND METHODS

CROSS REFERENCES TO RELATED APPLICATIONS

This application is a national phase of International Application No. PCT/162017/000925, filed Jun. 28, 2017, which claims the benefit of priority of U.S. Provisional Patent Application No. 62/355,375, filed on Jun. 28, 2016, and also claims the benefit of priority of U.S. Provisional Application No. 62/439,511, filed on Dec. 28, 2016. All of the foregoing applications are incorporated herein by reference in their entirety.

BACKGROUND

Technical Field

The present disclosure relates generally to systems and methods for treating air. Additionally, this disclosure relates to systems and methods for reducing an amount of one or more target gas species from a volume of treated air by dispersing a plurality of microbubbles through an aqueous air treatment solution.

Background Information

In some situations, a source of air may be contaminated as a result of the presence or generation of toxic gases, e.g., organic gases, organic vapors, organic mists, etc. Further, the source of air may be unfit for or undesirable for breathing in view of the presence of particulate matter or amounts of gases (e.g., partial pressures of gaseous species) that depart from standard atmospheric conditions. Such conditions may occur, for example, as a result of the presence of fire, especially in a closed environment, such as a building. Among other things, fire can contribute to increased levels of particulate matter, smoke, and carbon-based species (e.g., carbon monoxide, carbon dioxide, etc.), which can be harmful for breathing.

Fire protection systems are usually an extension of existing water distribution systems. Such systems may be inadequate in many situations (e.g., fires in tall buildings). Additionally, the deterioration of piping, sprinkler heads and hydraulics (the ability of the system to deliver water to design specifications) in fire protection systems can be present and cause reduced performance of fire safety equipment. Such deterioration may be attributed to the quality of the water being supplied from the water distribution source, including potable water distribution sources.

There is a need for fire safety equipment offering a decreased reliance upon water-based safety systems. There is also a need for equipment that can mitigate the risks of contaminated air produced by fire or any other condition resulting in air unsuitable or undesirable for breathing.

Protection from contaminated air can provide individuals that experience a fire or other situation with added time and capacity for escaping from the situation (e.g., inhabitants or workers in buildings may have more time to evacuate safely and may use existing facilities (elevators) for doing so). Such protection, which may be realized by the presently disclosed embodiments and their ability to provide safe-to-breathe air, can also protect individuals that must stay on site during hazardous air situations (e.g., building control room personnel, firefighters, etc.). The presently disclosed embodiments can be effective in treating air to remove one or more gaseous species or particulates produced by fire. The presently disclosed embodiments, however, may also be useful for treating air from any environment in order to change the character of the air (e.g., reduce a level of a target gas species, reduce levels of carbon-containing species, reduce levels of particulates, reduce levels of biological agents, reduce levels of toxic constituents, etc.).

SUMMARY

An air treatment unit may include an air inlet to receive a flow of input air for treatment and a reaction reservoir configured to hold an aqueous air treatment solution. The air treatment unit may also include an air dispersing element flow connected with the air inlet, wherein the air dispersing element is configured to convert at least a portion of the flow of input air into a plurality of microbubbles for introduction into the aqueous air treatment solution, such that an amount of one or more target gas species contained within the plurality of microbubbles is reduced through reaction with the aqueous air treatment solution. The unit may include an air outlet configured to output treated air from the reaction reservoir.

A method of treating air with an air treatment unit may include flowing air to be treated into an air inlet of a reaction reservoir, wherein the reaction reservoir includes an air treatment solution including a mixture of hydrogen peroxide and alkali hydroxide. The method may also include converting at least a portion of the flow of air to be treated into a plurality of microbubbles using an air dispersing element; introducing the microbubbles into the air treatment solution, such that an amount of one or more target gas species contained within the plurality of microbubbles is reduced through reaction with one or more constituents of the air treatment solution; and outputting treated air from the reaction reservoir.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings:

FIG. 1 is a diagrammatic representation of an air treatment unit according to an exemplary disclosed embodiment.

FIG. 2 provides a diagrammatic representation of an air dispersing element according to an exemplary disclosed embodiment.

FIG. 3 provides a perspective view representation of an air treatment unit according to an exemplary disclosed embodiment.

FIG. 4 provides a perspective view of an air treatment system, including an air treatment unit, according to exemplary disclosed embodiments.

FIG. 5 provides another perspective view of an air treatment system, including an air treatment unit, according to exemplary disclosed embodiments.

FIG. 6 shows a diagrammatic representation of another thermocatalytic converter according to exemplary disclosed embodiments.

FIG. 7 provides a cut-away perspective view of the thermocatalytic converter shown in FIG. 6.

FIG. 8 provides a diagrammatic representation of an air treatment system incorporated with an elevator system, according to exemplary disclosed embodiments.

Figure 9:
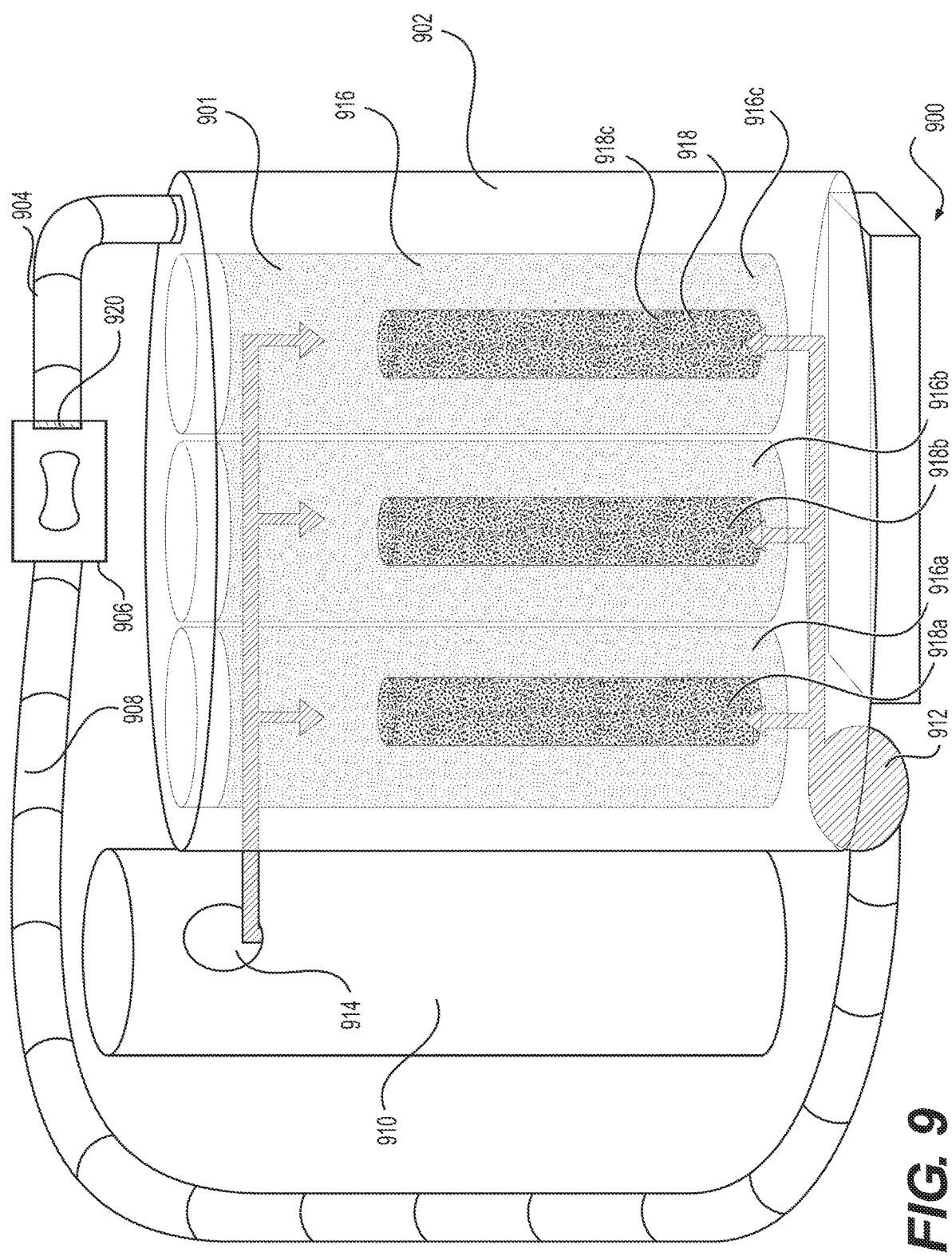

FIG. 9 provides a diagrammatic representation of a personal breather system, according to exemplary disclosed embodiments.

DETAILED DESCRIPTION

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

An air treatment unit may serve as a central component of the presently disclosed embodiments. FIG. 1 provides a block diagram representation of an air treatment unit 100 according to an exemplary disclosed embodiment. Air treatment unit 100 may include an air inlet 102 to receive a flow of input air for treatment. Air treatment unit 100 also includes a reaction reservoir 104 configured to hold an aqueous air treatment solution. An air dispersing element 106 may be flow connected with the air inlet (e.g., either via a direct flow connection or via an indirect connection including one or more intervening conduits, treatment elements, pumps, or any other device or unit for enabling a flow of air). Air dispersing element 106 may be configured to convert at least a portion of the flow of input air into a plurality of microbubbles 108 for introduction into the aqueous air treatment solution 110, which can reduce an amount of one or more target gas species contained within the plurality of microbubbles through reaction with the aqueous air treatment solution. As used here, the term microbubble may refer to any bubble of air to be treated having a diameter of less than one millimeter. Air treatment unit 100 may also include an air outlet 112 configured to output treated air from reaction reservoir 104.

Figure 2:
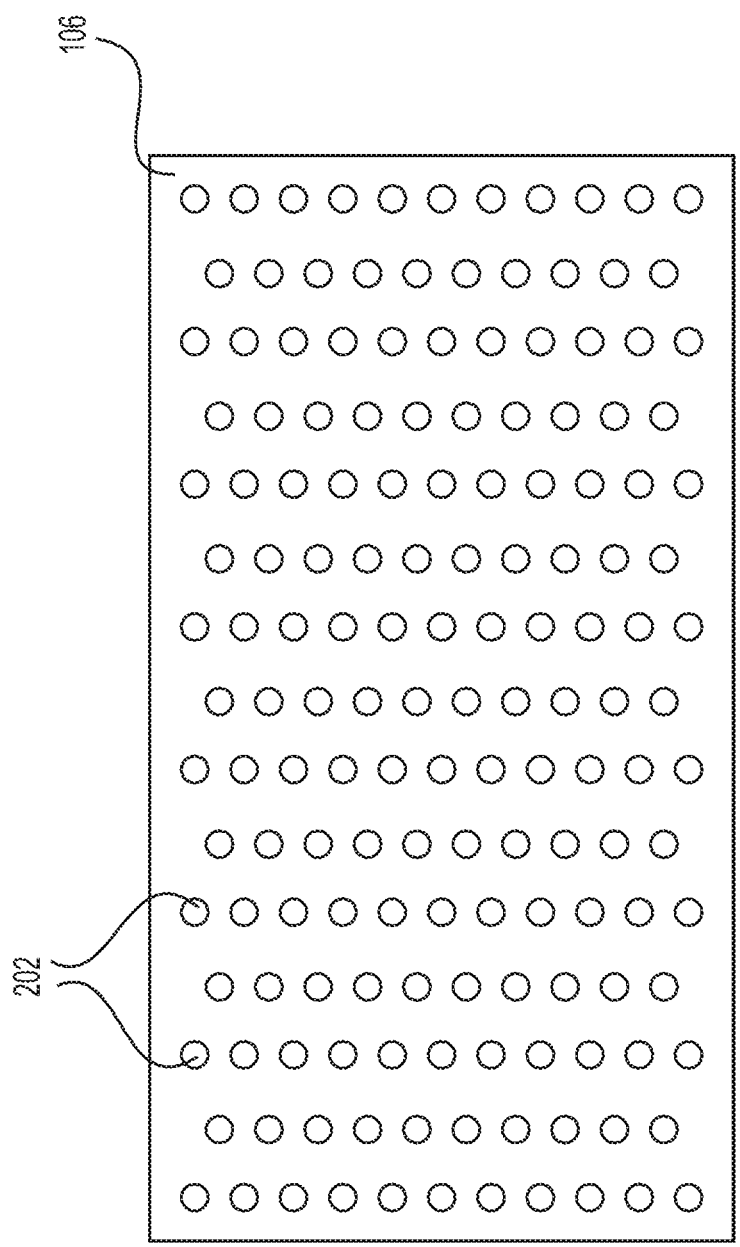

Air dispersing element 106 may include any suitable structure for receiving a flow of input air to be treated and providing at least a portion of the air to be treated to reaction reservoir 104 in the form of a plurality of microbubbles 108. FIG. 2 provides a diagrammatic top-view representation of an air dispersing element 106 according to an exemplary disclosed embodiment. As shown, air dispersing element 106 may include a plurality of holes 202 for emitting microbubbles 108 into reaction reservoir 104.

The plurality of holes 202 may include any suitable size or shape and may be arranged in any suitable distribution pattern in order to provide microbubbles having a desired set of characteristics. For example, the size (e.g., diameter) of the holes in air dispersing element 106 may be related to the diameter of microbubbles produced in reaction reservoir 104. As the hole size is increased, the size of the microbubbles may also increase. Additionally, the distribution pattern of the plurality of holes on air dispersing element 106 may contribute to whether and how the emitted microbubbles interact with one another. Holes that are closer together may result in a greater number of microbubble-to-microbubble collisions as compared to holes that are spaced farther apart. Additionally, holes that are closer together may result in a greater number of mergers between microbubbles, which can greatly reduce reaction efficiency by reducing a ratio between available reaction surface area and bubble volume.

In some embodiments, the plurality of holes may include an average diameter of between 0.5 microns and 500 microns. In other embodiments, the plurality of holes may have an average diameter of between 10 microns and 100 microns.

Regarding hole spacing, some embodiments may include a plurality of holes in air dispersing element 106 that are separated from one another by an average distance that is between two times and 30 times an average diameter of the plurality of holes. In other embodiments, the plurality of holes may be separated from one another by an average distance that is between six times and eight times an average diameter of the plurality of holes. In some embodiments, the plurality of holes may be distributed across at least a portion of the air dispersing element 106 with a distribution density of between one and 100 holes per square centimeter. In other embodiments, the plurality of holes may be distributed across at least a portion of the air dispersing element 106 with a distribution density of between three and seven holes per square centimeter.

Such diameter ranges, separation distances, and/or distribution distances can have important effects on the performance of air treatment unit 100. For example, holes that are sized, spaced, and distributed within the ranges described above may provide benefits such as high operating flow rates of air to be treated (e.g., between 300 liters/min and 600 liters/min, or more) and may offer significantly improved air treatment performance (e.g., by increasing surface area and decreasing diffusion distances to improve interaction between gaseous species contained in the microbubbles and the aqueous treatment solution in reaction reservoir 104) as compared to bubbles having diameters greater than one millimeter or that are spaced more farther apart (tending to decrease flow rate) or closer together (tending to result in more bubble-to-bubble collisions and combining of bubbles into larger bubbles that decrease the overall available surface area for reaction). It has been found, for example, that bubbles having a diameter of 200 microns may be up to about 300 times less efficient in air treatment than bubbles having a diameter less than 100 microns and may be nearly as inefficient in air treatment as bubbles having a diameter of 1 mm.

The relationship between bubble size and system performance may be further illustrated by comparing the surface of a single spherical bubble with a radius of 1 cm to the same volume of air divided into 106 spherical bubbles with a radius of 100 microns. In the case of a single bubble, the surface area of the bubble will be approximately 12.567 $cm^2$, while the total surface area of the microbubbles will be approximately 1,256 $cm^2$, a ratio of 1:100. This may have a direct effect on the solubility of gases in the medium of the active solution and may have a direct effect on the rate of reaction and conversion of the reaction. According to diffusion laws, the average time required for a molecule to pass a given distance increases with the square of the distance (due to random collisions with other molecules). Consequently, the time required for a molecule to travel from the center of a bubble with a diameter of 1 cm to its surface is 10,000 times greater than the time it takes when the diameter is 100 microns. The use of small bubbles may have other significant advantages. For example, the ratio of the volume of the bubble to its surface area is proportional to its radius (assuming a spherical bubble). Therefore, the smaller the bubbles, for a given unit of time, a larger percentage of the gas volume inside the bubble may react with the solution.

The air dispersing element 106 may be fabricated from any suitable material. The air dispersing element may be made from metals, polymers, etc. In one embodiment, air dispersing element 106 may be made from a stainless steel foil, membrane, etc. The thickness of the air dispersing element may be selected from various values. In some embodiments, the air dispersing element has a thickness within a range of 10 microns to 500 microns (preferably about 100 microns). In some embodiments, air dispersing element 106 may be at least partially coated with nickel.

Air dispersing element 106 is configured to produce microbubbles of air to be treated in reaction reservoir 104. As noted, the characteristics of the microbubbles can significantly impact performance of the air treatment unit in reducing a level of a gaseous species from air to be treated. For example, as the size of the microbubbles decreases, the surface area for potential reactions between the molecules within the bubbles and active agents of the aqueous air treatment solution may increase, and a diffusion distance between the molecules and the active agents may decrease. In some embodiments, air dispersing element 106 is configured to generate microbubbles having an average diameter of between 1 and 100 microns. In other embodiments, the air dispersing element may be configured to generate microbubbles having an average diameter of between 5 and 50 microns.

Regarding the distribution of diameters of microbubbles, the air dispensing element may produce highly uniform bubbles. In some cases, at least 80% of the microbubbles have an average diameter of between 10 microns and 70 microns. The properties of the microbubbles also contribute to the mean free path of the bubbles in the aqueous treatment solution. Longer mean free paths may increase an amount of time available for potential reactions between the molecules in the microbubbles and the active agents in the aqueous treatment solution. In some embodiments, the microbubbles generated by the air dispersing element may have a mean free path in the air treatment solution that ranges from 0.01 cm to 25 cm. In some embodiments, at least 80% of the microbubbles generated by the air dispersing element have a mean free path of at least 1 mm.

The aqueous solution included in reaction reservoir 104 may include any active agents suitable for reacting with and reducing an amount of one or more gaseous species within the air to be treated. In some embodiments, the aqueous treatment solution includes a combination of an oxidizing agent and an alkali hydroxide. In some cases, these constituents may react with one another to form a superoxide, which in turn reacts with gaseous species in the air to be treated. In some embodiments, the oxidizing agent may include one or more of hydrogen peroxide, permanganate, persulfate, or combinations thereof. The alkali hydroxide may include one or more of sodium hydroxide, calcium hydroxide, potassium hydroxide, lithium hydroxide, trisodium phosphate, tripotassium phosphate, triethanolamine, or combinations thereof.

Various ratios of oxidizing agent to alkali hydroxide may be suitable for use in the air treatment solution. In some embodiments, the air treatment solution has an oxidizing agent to alkali hydroxide ratio of at least 1:1 and up to 4:1. In other embodiments, the air treatment solution has an oxidizing agent to alkali hydroxide ratio of at least 1:1 and up to 1.6:1.

Similarly various concentrations of reagents may be used to provide the air treatment solution. In some embodiments, the aqueous air treatment solution includes hydrogen peroxide having a molarity of between 5M and 50M, preferably near 10M. The aqueous air treatment solution may also include alkali hydroxide having a molarity of between 3M and 30M. Together the agents comprising the aqueous air treatment solution may result in a pH for the aqueous air treatment solution of between 10 and 12.5.

In some embodiments, as discussed in more detail below, the aqueous air treatment solution includes a superoxide anion formed by reaction of the oxidizing agent (e.g., hydrogen peroxide, etc.) with at least one alkali hydroxide. The aqueous air treatment may further include a phase transfer catalyst, such as an ammonium salt or other suitable compound or material. The phase transfer catalyst may increase reaction surfaces available for reaction between molecules of the air to be treated and active agents (e.g., superoxide anions). Not only can a phase transfer catalyst affect the number of available reaction sites, but it may also alter the density profile of the aqueous treatment solution to increase a length of time that the microbubbles remain in the aqueous treatment solution—a factor that can significantly improve treatment efficiency even for increases in time on the order of nanoseconds, microseconds, etc.

Air treatment unit 100 may reduce an amount of one or more gaseous species through various reactions occurring, e.g., between superoxide anions present in the air treatment solution and gases within the microbubbles percolating through the solution. For example, carbon monoxide may react with an alkaline solution according to one or two of the representative reactions below in which hydrogen is produced from a reaction of carbon monoxide, sodium hydroxide and water. Sodium bicarbonate, or sodium carbonate, may also be produced as one of the by-products according to the following reactions:

$$CO+2NaOH \leftrightarrows Na_2CO_3+H_2;$$

$$CO+NaOH+H_2O \leftrightarrows NaHCO_3+H_2.$$

In additional exemplary embodiments, nitrogen dioxide may react with an alkaline solution according the following reaction:

$$2NO_2+2NaOH \leftrightarrows NaNO_2+NaNO_3+H_2O.$$

In additional exemplary embodiments, HCN may react with an alkaline solution according the following reaction:

$$HCN+NaOH \rightarrow NaCN+H_2O.$$

Carbon monoxide may be removed from a gas stream using wet scrubbing methods where the liquid employed to capture the CO comprises aqueous alkali hydroxide and hydrogen peroxide and also a phase transfer catalyst. Carbon monoxide undergoes swift mineralization into the corresponding water soluble alkali carbonate according to the following reaction (where M stands for the alkali metal, e.g. sodium or potassium):

$$2MOH+3H_2O_2+CO \rightarrow M_2CO_3+4H_2O+O_2$$

Based on this equation, oxygen is generated as a beneficial by-product. Notably, the mineralization of carbon monoxide is achieved in the absence of a CO-removal catalyst. The presently disclosed systems, therefore, may include a method of removing carbon monoxide from a gas stream, comprising bringing the gas stream into contact with an aqueous solution where alkali hydroxide and hydrogen peroxide are combined together, preferably in the presence of a phase transfer catalyst.

Carbon monoxide is absorbed into the aqueous MOH/$H_2O_2$ solution, and its oxidation takes place under highly alkaline conditions. That is, a concentrated solution of alkali hydroxide is used, say, with a molarity of not less than 3M, preferably not less than 5M and even more preferably, above 6M (from 6 to 10M). For example, sodium hydroxide solution with weight concentration in the range between 20 to 30% may be used (20-30 g per 100 g water). As to hydrogen peroxide, commercially available solutions commonly employed in chemical industries, such as a 30% solution (containing 30 g $H_2O_2$ per 100 g water) or higher grade solutions are all suitable for use in the invention.

The two reagents ($H_2O_2$ and MOH) are combined together in the aqueous solution such that the molar ratio $H_2O_2$:OH— is not less than 1:1, e.g., not less than 1.2:1, for example, in the range from 1.2:1 to 3:1, more specifically from 1.4:1 to 2.5:1. Removal of carbon monoxide from the gas is generally enhanced upon gradual addition of hydrogen peroxide solution to the base solution while simultaneously forcing the gas to contact the resulting mixed reagents.

Another process variable which may be adjusted to enhance CO removal is the temperature of the reaction medium: the lower the temperature, the higher the solubility of the gas in the aqueous solution. Consequently, better efficiency may be achieved on contacting the gas and the aqueous reagent at a relatively low temperature, e.g., in the range from 5 to 80° C. Hence, the temperature of the gas stream may be reduced by means of passing it through a heat exchanger prior to its feeding to the aqueous solution; or the temperature of the aqueous solution may be properly controlled.

Hydrogen peroxide reacts with hydroxyl groups to generate various radicals with strong oxidative properties and the addition of a phase transfer catalyst (PTC) serves the purpose of minimizing the loss of these active species, on account of the ability of PTC to exchange ions with the aqueous phase. The phase transfer catalyst of choice is preferably selected from the group consisting of onium salts, especially ammonium salts, in particular aliphatic quaternary ammonium salts. These salts have a nitrogen-containing cation, e.g., a quaternary ammonium cation, namely, $N^+R_1R_2R_3R_4$ wherein each of $R_1$, $R_2$, $R_3$ and $R_4$ is independently C1-C18 alkyl group (preferably C1-C12 alkyl, which may be either linear or branched, most preferably linear) and a counter anion, e.g., halide anion such as chloride or bromide. Especially preferred are quaternary ammonium salts of the formula $N^+CH_3[(CH_2)kCH_3]_3Hal^-$, wherein k is at least 5, e.g., between 5 to 9, and Hal is chloride or bromide. As an example of this preferred sub-class of quaternary ammonium salts, methyltrioctyl ammonium halide can be mentioned (k=7), which is commercially available in the form of its chloride salt as Aliquat 336. Other examples include didodecyldimethylammonium bromide (DDAB); hexadecyltrimethylammonium bromide (CTAB); and tetraoctylammonium bromide (TOAB). The weight ratio between the MOH solution and the PTC is from 1:0.01 to 1:0.3, preferably from 1:0.05 to 1:0.1.

The separation of carbon monoxide could be achieved by scrubbing the gas with the liquid described above (aqueous $H_2O_2$/MOH and optionally PTC) in a gas-liquid contactor. To this end, many possible designs of wet scrubbers could be used, including a packed bed scrubber, a spray scrubber, a plate scrubber and a venturi scrubber.

Mixing of the oxidizing agent (e.g., hydrogen peroxide, etc.) with an alkali hydroxide may result in generation of a superoxide radical anion. Such a superoxide may react with carbon-containing materials to form a carbonate salt. In some cases, hydrogen peroxide may be used as an oxidizing agent in a concentration of at least 10M, e.g., between 10M and 30M or up to 50M. The concentrations and relative amounts of oxidizing agent and the alkali hydroxide may be adjusted such that the reaction results in the formation of the superoxide radical anion $0_2^-$ by the following sequence of reactions:

$$2MOH+H_2O_2 \rightarrow M_2O_2+2H_2O \qquad (I)$$

$$M_2O_2+2H_2O_2 \rightarrow 2MO_2+2H_2O \qquad (II)$$

wherein M denotes the alkali metal (e.g., sodium, potassium, etc.). The superoxide anion rapidly reacts with carbon-containing species (e.g., carbon dioxide, carbon monoxide, etc.) to produce salt-based reaction products.

The aqueous air treatment solution included in reaction reservoir 104 may be provided or made in various ways. In some cases, e.g., where the active species of the aqueous solution may coexist without significant reaction, the aqueous solution may be pre-loaded into reaction reservoir 104 during manufacture, during installation, etc. In other cases, including those in which the aqueous solution is comprised of an oxidizing agent (e.g., hydrogen peroxide, etc.) that reacts with an alkali hydroxide to form superoxide anions that react with gaseous species in the air to be treated, mixing of the constituents initiates a reaction that creates the superoxide anions. Such a mechanism may be advantageous in that the reagents may be combined only when needed and in amounts needed. In this way, reagents may be preserved, which can lengthen an operating life of the aqueous treatment solution (especially in cases (e.g., personal breathing apparatuses) where the amounts of reagents available for creating the air treatment solution may be limited).

Air treatment unit 100 may include various configurations for enabling generation of the aqueous solution and/or adjustment of the characteristics of the solution. For example, as shown in FIG. 1, air treatment unit 100 may include a water reservoir 120 for providing a supply of water to reaction reservoir 104. Air treatment unit 100 may also include an oxidizing agent reservoir 124 and an alkali hydroxide reservoir 122 for providing supplies of oxidizing agent and alkali hydroxide, respectively, to the reservoir. Reservoirs 122 and 124 may store reagents in liquid form or in solid form. Further, the supply of reagents to the reaction reservoir may be accomplished via fluid flow or through any type of mechanical transfer. In some embodiments, an oxidizing agent, such as hydrogen peroxide, may be flowed or provided from reservoir 124 through a first reagent inlet 160. An alkali hydroxide agent may be flowed or provided from reservoir 122 through a second reagent inlet 162. Water may be supplied to reaction reservoir 104 through water inlet 164.

In some embodiments one or more constituents of the aqueous treatment solution (e.g., water and the alkali hydroxide) may be preloaded into reaction reservoir 104, and subsequent to a determination that air to be treated is available, the treatment solution may be activated through addition of at least some of the oxidizing agent (e.g., hydrogen peroxide, etc.). In other cases, more than one of the available reagents, including the oxidizing agent and the alkali hydroxide, may be supplied to the reaction reservoir on an as needed basis in response to information obtained from one or more sensors.

In some embodiments, the air treatment unit 100 may include a controller 126 and one or more sensors, including for example, air sensors 128, 130, 132; pH sensor 134; and fluid level sensor 136. Air sensors 128, 130, and/or 132 may generate outputs indicative of a level of at least one constituent in a volume of air. As shown, sensor 132 may monitor air quality of air within inlet 102, or at any other location upstream from reaction reservoir 104. Sensor 130 may monitor air quality of air within inlet 112, or at any other location downstream from reaction reservoir 104. And sensor 128 may monitor air quality at a location remote from the air treatment unit (e.g., in an elevator shaft, room, hallway, etc. within a building or at any location in an environment either indoors or outdoors).

Controller 126 may be based on any type of logic device that can be programmed with instructions for enabling the controller to accomplish the specific functions described herein (e.g., using discrete instructions, neural networks, etc.). Controller 126 may include one or more microprocessors, logic gate arrays, preprocessors, CPUs, support circuits, digital signal processors, integrated circuits, memory, or any other types of devices suitable for running applications including the programmed instructions and for analysis of input signals. In some embodiments, controller 126 may include any type of single or multi-core processor, central processing unit, etc. Various processing devices may be used, including, for example, processors available from manufacturers such as Intel®, AMD®, etc. and may include various architectures (e.g., x86 processor, ARM®, etc.).

Various aspects of the aqueous treatment solution may be actively adjusted under command of the controller based on monitored outputs of these (and any other) sensors. For example, in some embodiments, controller may monitor the output of any of air quality sensors 130, 132, and/or 128 to determine a level (or any indicator of a level) of at least one constituent in air monitored by the respective sensor. If the level is determined to exceed a predetermined threshold, controller 126 may cause one or more actions to generate an air treatment solution within reaction reservoir 104 configured to react with the monitored constituent (or any other constituent(s) of a volume air to be treated). For example, controller 126 may initiate transfer into the reaction reservoir 104 of a supply of hydrogen peroxide (or other oxidizing agent) via first reagent inlet 160. Such transfer may be effected through control of one or more controllable flow components (e.g., pumps, valves, etc.). In some embodiments, controller 126 may also initiate transfer into the reaction reservoir 104 of a supply of alkali hydroxide via the second reagent inlet 162. Further, controller 126 may cause initiation of a flow of air to be treated into inlet 102 through control of various pumps, gate valves, fans, vents, etc. Notably, the output of air sensor 132 (in air inlet 102) or of air sensor 128 (in an environment remote from air treatment unit 100) may be useful for determining when to initiate operation of air treatment unit 100. For example, one or more of these sensors may monitor for the rise of conditions (e.g., fire, chemical contamination, etc.) under which air treatment may be desired. If, for example, air sensor 128 (located, e.g., in an elevator shaft, room, hallway, etc. within a building or at any location in an environment either indoors or outdoors) determines that one or more target gaseous species are present and reduction or removal of those target species is desired, then that information provided by air sensor 128 may be used to initiate operation of the air treatment unit or any system in which the air treatment unit is included. Air sensor 130, positioned in outlet 112 of air treatment unit 100 may be useful as a feedback device for controller 126. For example, sensor 126 may enable controller 126 to monitor a level of a chemical species (e.g., CO, etc.) in the output of the air treatment unit (post-treatment). If the level exceeds a predetermined level (e.g., 100 ppm), then controller 126 can adjust a characteristic of the aqueous treatment solution by, for example, adding to the reaction reservoir 104 one or more of a portion of the oxidizing agent from reservoir 124 and/or a portion of the alkali hydroxide from reservoir 122.

As indicated above, air treatment unit 100 may include a pH sensor 134 configured to provide an output indicate of a pH level associated with aqueous treatment solution 110. Controller 126 may monitor the output of the pH sensor 134 to determine a pH level of the solution in the reaction reservoir 104. Controller 126 may also determine how the pH level of the solution in the reaction reservoir compares to a target pH level or pH value range (e.g., between 10 and 12.5). If controller 126 determines that the pH level of the solution in the reaction reservoir 104 differs from the target pH level by more than a threshold difference (or falls outside of a desired range), controller 126 may initiate transfer into the reaction reservoir of at least one of the supply of hydrogen peroxide via the first reagent inlet or the supply of alkali hydroxide via the second reagent inlet.

Air treatment unit 100 may also include various other sensors for enabling control of different aspects of the unit. In some embodiments, air treatment unit 100 may include a fluid level sensor 136 configured to generate an output indicative of a fluid level of a solution in the reaction reservoir 104. Controller 126 may sample the output of the fluid level sensor and, if the controller determines that that a fluid level in the reaction reservoir has fallen below a target fluid level, controller 126 may initiate transfer into the reaction reservoir of additional fluid. For example, controller 126 may cause one or more flow control actuators (e.g., valves, pumps, etc.) to initiate a flow of fluid from the oxidizing agent reservoir 124 (through inlet 160), the alkali hydroxide reservoir 122 (through inlet 162), the water reservoir 120 (through a water inlet 164), or from any combination of these reservoirs or others that may be associated with air treatment unit 100.

The characteristics of the air treatment unit 100 described above can provide several desirable performance characteristics. Not only may the unit be highly effective at reducing levels of unwanted particulates and gaseous species from a flow of input air, but because of the wet or semi-wet scrubbing components of air treatment unit 100, the unit may be effective at cooling air and providing an output air stream that less than 40 degrees Celsius, even in situations where the input air to be treated exceeds 100 degrees Celsius or more. In some cases, air treatment unit 100 may reduce a temperature of the input air by at least a factor of two (or more). Further, the air dispersing element of the presently disclosed embodiments may be effective at generating microbubbles that enable orders of magnitude reductions in levels of gaseous species from input air to be treated. In some cases, levels of CO present in the input air to be treated may be reduced by at least a factor of 100. Additionally, the air dispersing element 106 may enable high flow rates through air treatment unit of between 300 and 600 liters per minute (or higher). Such flow rates may make air treatment unit 100 especially suited for large scale air treatment systems, such as those configured for treating air supplied to elevator cabins. Specifically, flow rates at this level can create an overpressure in an environment (e.g., an elevator cabin) that can prevent entry of air into the environment from sources other than the air treatment system (e.g., through seams, cracks, vents, holes, etc. in an environment).

Figure 3:
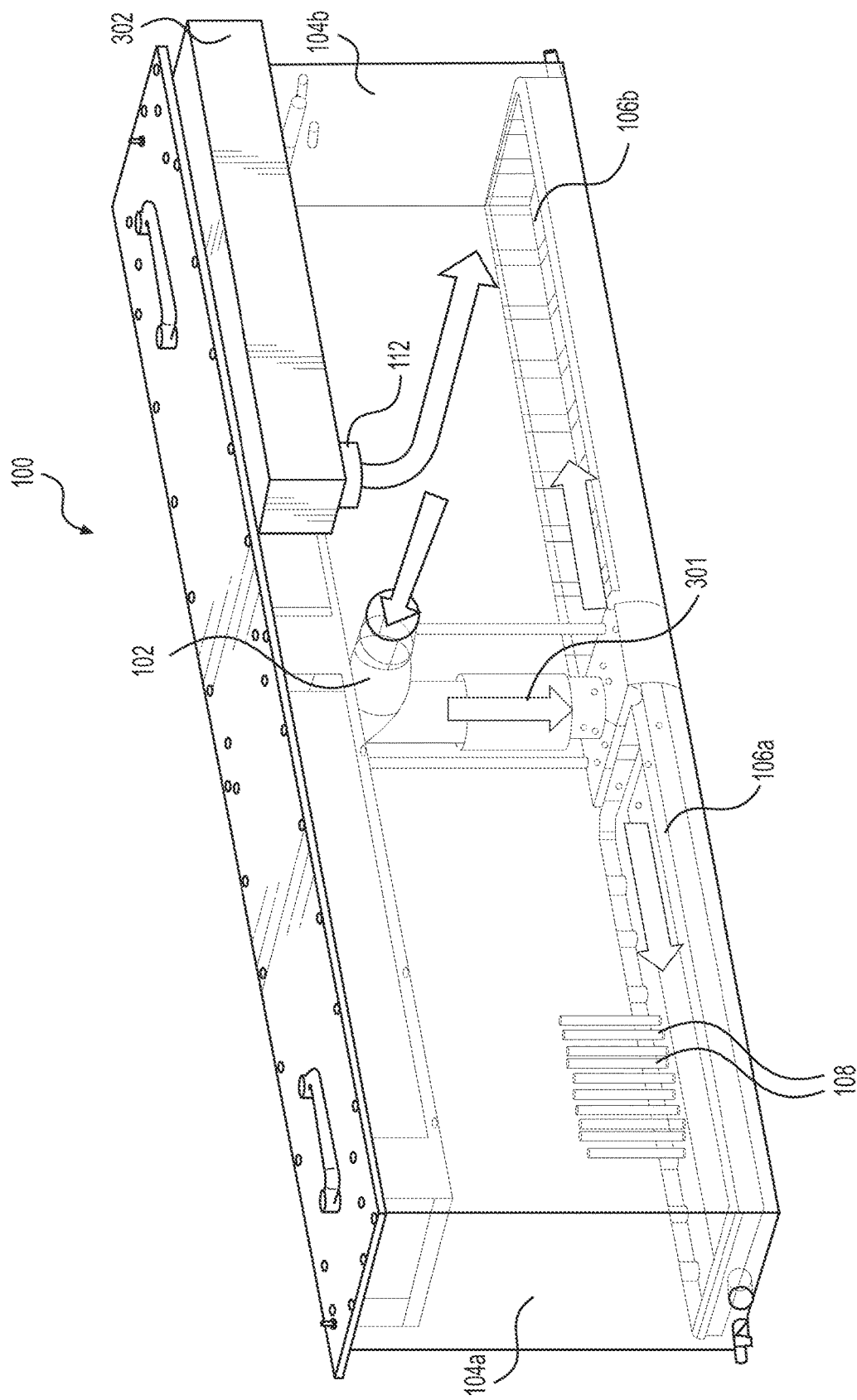

FIG. 3 provides a perspective view representation of an air treatment unit 100 according to an exemplary disclosed embodiment. In the embodiment shown in FIG. 3, air treatment unit is configured with a modular design to facilitate inclusion of air treatment unit 100 as part of a broader air treatment system. As depicted, air treatment system 100 includes air inlet 102 and air outlet 112. A flow of air to be treated enters air inlet 102 and may be diverted and/or separated into multiple paths each associated with one or more treatment components. As shown, an input air flow 301 is divided into two paths, each flowing to a different section of reaction reservoir 104. For example, one portion of air flow 301 may be provided to a first air dispersing element 106a to generate microbubbles 108 within a first zone 104a of the reaction reservoir. Similarly, another portion of air flow 301 may be provided to a second air dispersing element 106b (shown without its microbubble foil/membrane) to generate microbubbles within a second zone 104b of the reaction reservoir.

As microbubbles 108 move through the aqueous air treatment solution within reaction reservoir 104 (upward, in the example shown in FIG. 3), gas molecules within the microbubbles can react with active species of oxygen in the solution. For example, CO or other carbon-containing species may react with superoxide anions present in the solution. As a result, gas within the microbubbles may be depleted of certain gaseous species and may be collected as treated air. Prior to exiting the air outlet 112, the treated air may be conditioned by one or more conditioning units included, for example, within a conditioning module 302. In some embodiments, conditioning module 302 may include a condenser (optional) having a surface cooler than the treated air such that aqueous treatment solution or any of its liquid constituents carried by the treated air may be condensed and collected. The collected liquid may be returned to the reaction reservoir 104. Conditioning module 302 may also include a filter, screen, or any other type of structure to reduce/eliminate or separate froth or foam from the flow of treated air.

Figure 4:
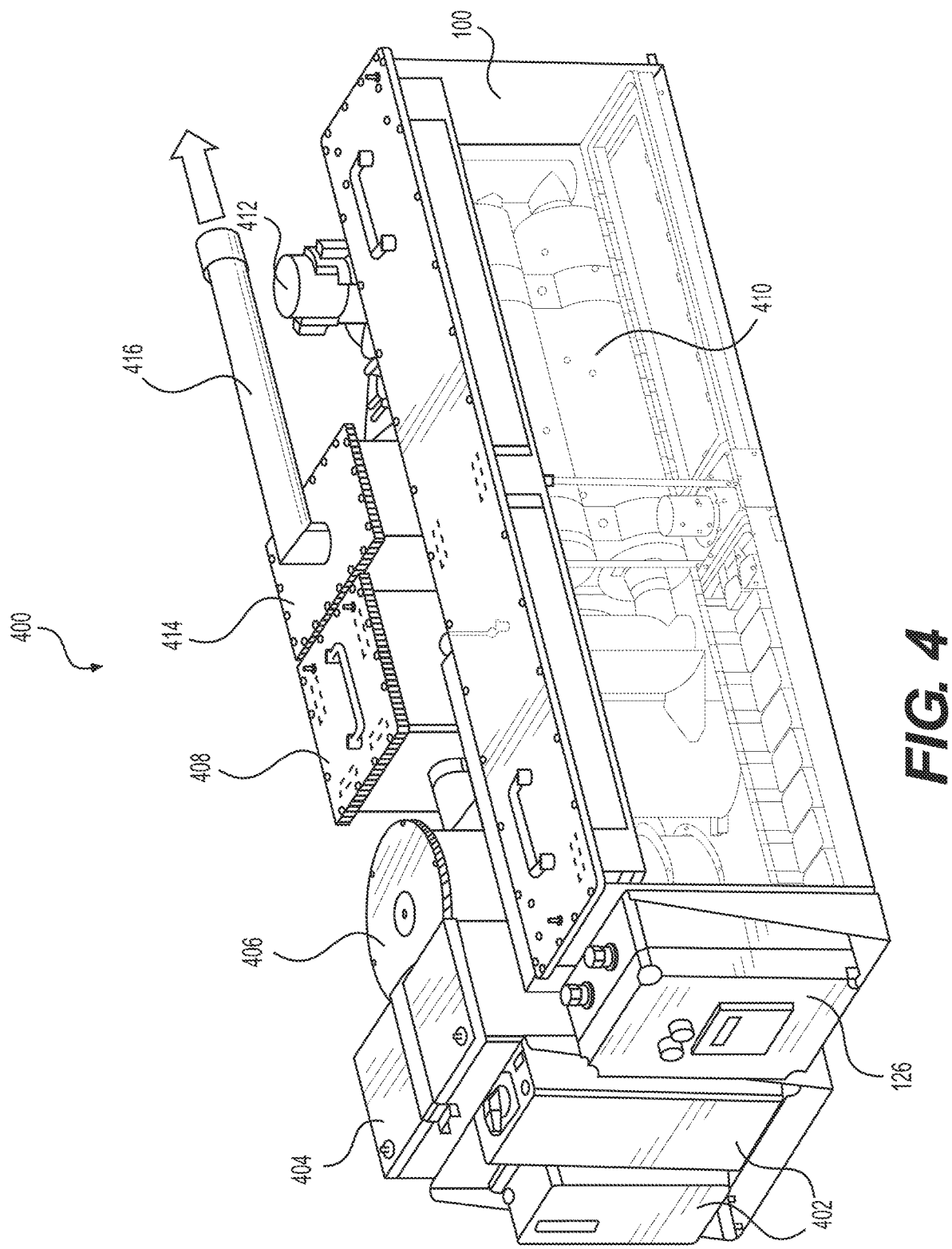
Figure 5:
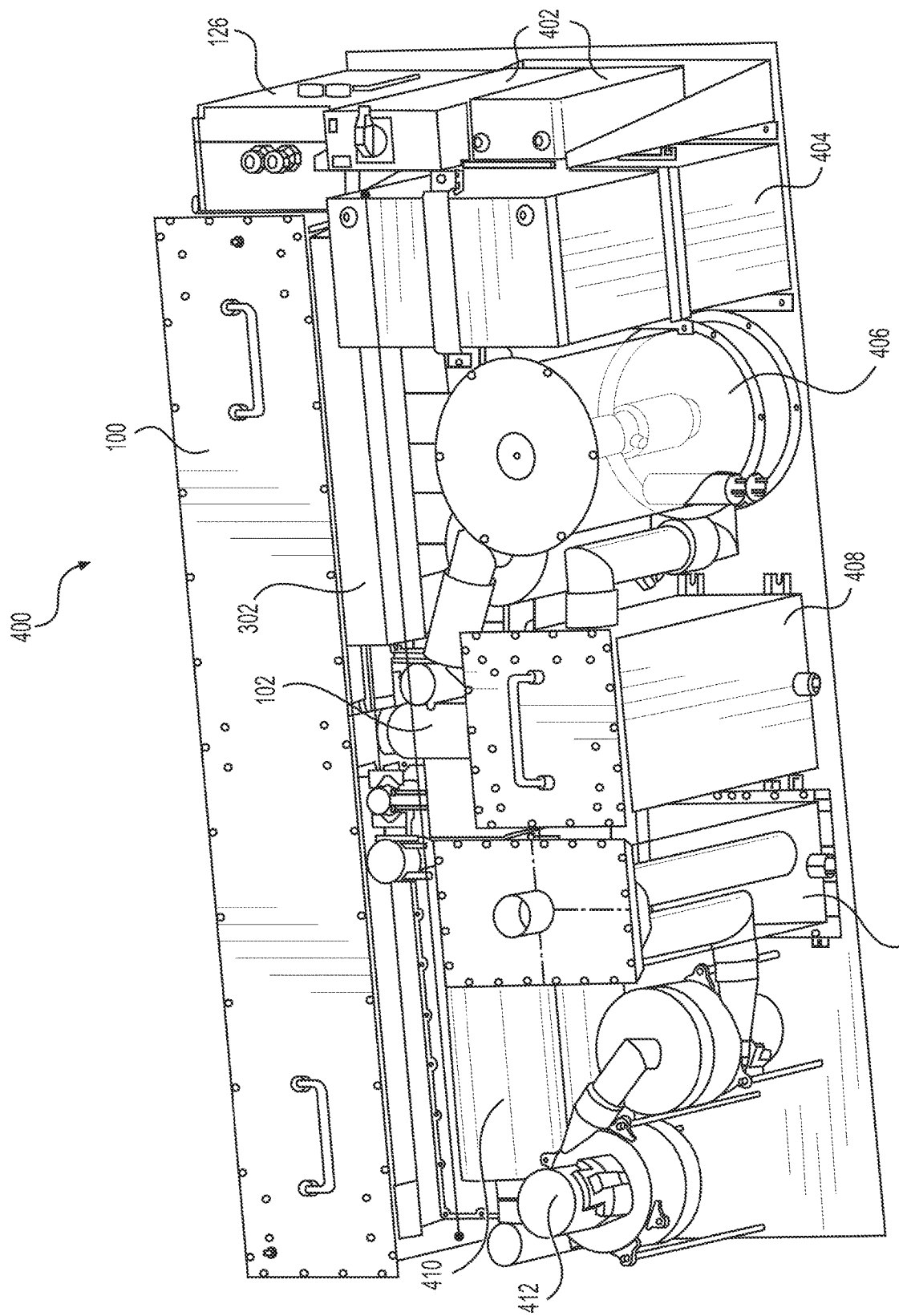

Air treatment unit 100 may be included as a component of a larger assembly. For example, FIG. 4 provides a perspective view of an air treatment system 400 that includes air treatment unit 100 as one of its modules. Air treatment system 400 may include controller 126, a controls and communications module 402, and one or more batteries 404. Input air to be treated may flow into a thermocatalytic converter 406 before traveling to an initial stage converter 408. Air exiting from the initial stage converter 408 may be provided to air treatment unit 100, which may also be referred to as a main converter. Treated air provided at the outlet of air treatment unit 100 may flow through one or more filters 410 (e.g., certified dry CBRN filters which may enable certification of system 400 as compliant with CBRN defense requirements) before being provided to a cooling stage 414 and then to a final outlet 416. Air treatment system 400 may include more or fewer components for treating air depending on a particular application. In some embodiments, especially where the input air to be treated may have high levels of particulates (e.g., air contaminated as a result of fire), air treatment system may include one or more particulate filters integrated with any of the components shown in FIG. 4 or as one or more standalone filtering modules. FIG. 5 provides another perspective view of air treatment system 400, different from the perspective provided by FIG. 4.

Air treatment system may include one or more pumps 412 and/or blowers to cause air to flow through air treatment system 400. Pumps 412 may be positioned at any point along the flow path associated with air treatment system 400. For example, one or more pumps may be located at an inlet to air treatment system 400 upstream from thermocatalytic converter 406, at outlet 416, or anywhere in between. One or more pumps 412 may be positioned in the flow path downstream of air treatment system 100 and/or downstream of filters 410. Placing the pumps at or near the end of the flow path of air treatment system may help ensure that air drawn into pumps 412 is relatively cool, free of particulates and potentially damaging gaseous species, as such contaminants may have been reduced or removed by the air treatment modules upstream from the pump or pumps. In this way, the operational life of the pump or pumps may be extended. Pumps 412 may include any combination of positive or negative (e.g., vacuum) pressure pumps designed to "push" or "pull" and air flow. In this way, one or more pumps may be positioned to draw air through air treatment system or any of its components or to push air into air treatment system or any of its components.

Control and communications module 402 may include one or more processing devices for assisting controller 126 with automatic control of the various controllable features of air treatment system. In some embodiments, the communications portion of module 402 may establish a wired or wireless connection with one or more components of air treatment system 400 or one or more systems located remotely with respect to air treatment system 400. For example, module 402 may establish a Wi-fi, Bluetooth, cellular, and/or Ethernet (or any other type of wired or wireless data connection) with one or more sensors (e.g., air quality sensors, smoke sensors, temperature sensors, etc.), the Internet, or any other source of information. Module 402 may provide periodic transmission of an "alive" messages to a control center that would monitor the operational and/or maintenance status of a plurality air treatment systems, for example, in multiple installations. Technicians may be dispatched based on this information. An indication that a system 400 activated and went into action could also be conveyed to an appropriate dispatcher who could alert first responders of the event.

Thermocatalytic converter 406 may heat air flowing to air treatment system 400 and may perform an initial treatment of the air flow. Thermocatalytic converter 406 may include a heater configured to heat air passing therethrough to a temperature in the range of 80 degrees Celsius to 500 degrees Celsius. Thermocatalytic converter 406 may also include a catalytic converter configured to receive the heated air. The heater may be powered, for example, by at least one of electric power or fuel gas combustion.

A fuel gas heater may provide heat through combustion of one or more fuel gases including, for example, methylacetylene, propadiene, propane, butane, propylene, ethane, or a mixture thereof. An electric heater may comprise an electrically resistive material which heats when an electric current flows therethrough. Suitable electrically resistive materials include but are not limited to: semiconductors such as doped ceramics, electrically conductive ceramics (such as, for example, molybdenum disilicide), carbon, graphite, metals, metal alloys and composite materials made of a ceramic material and a metallic material.

Figure 6:
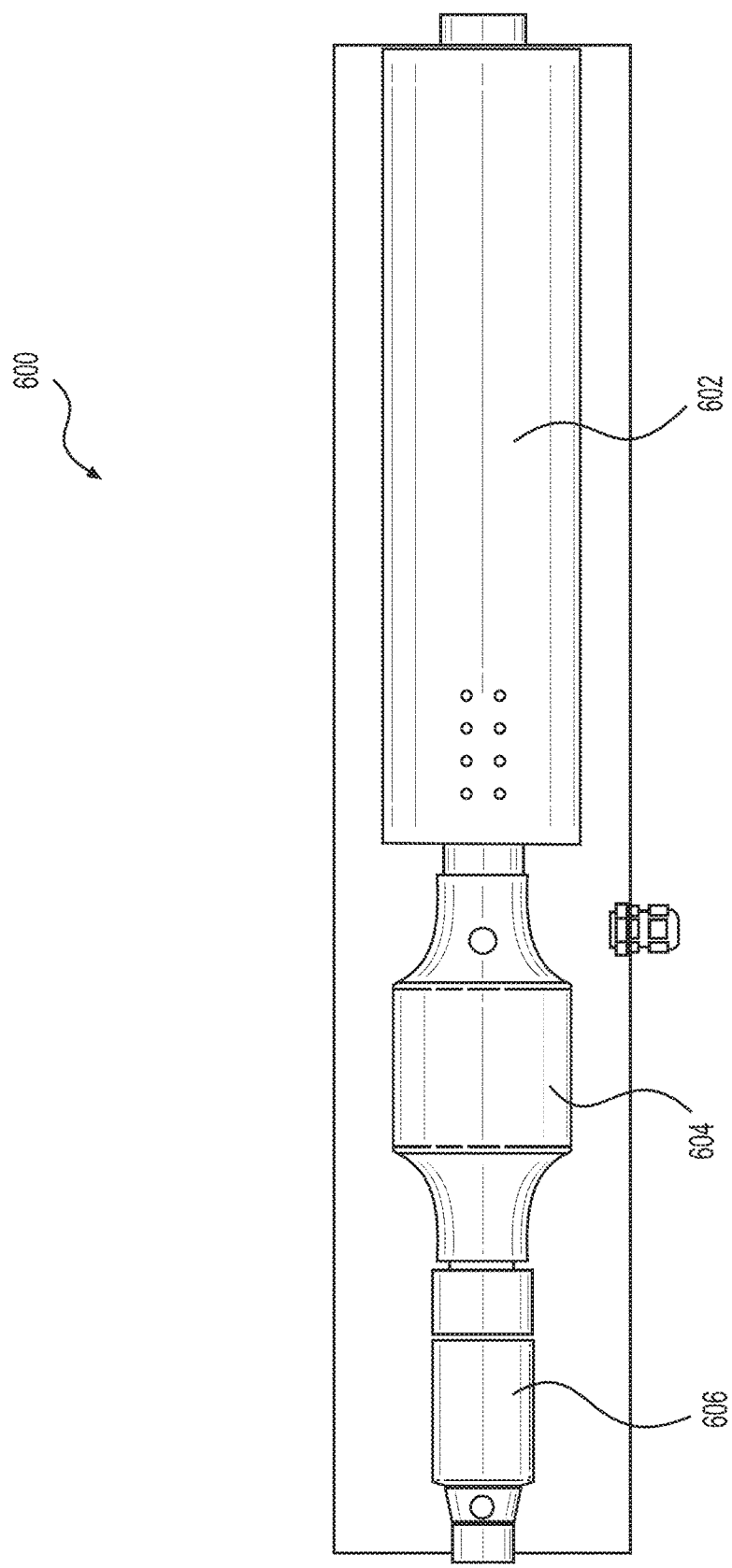
Figure 7:
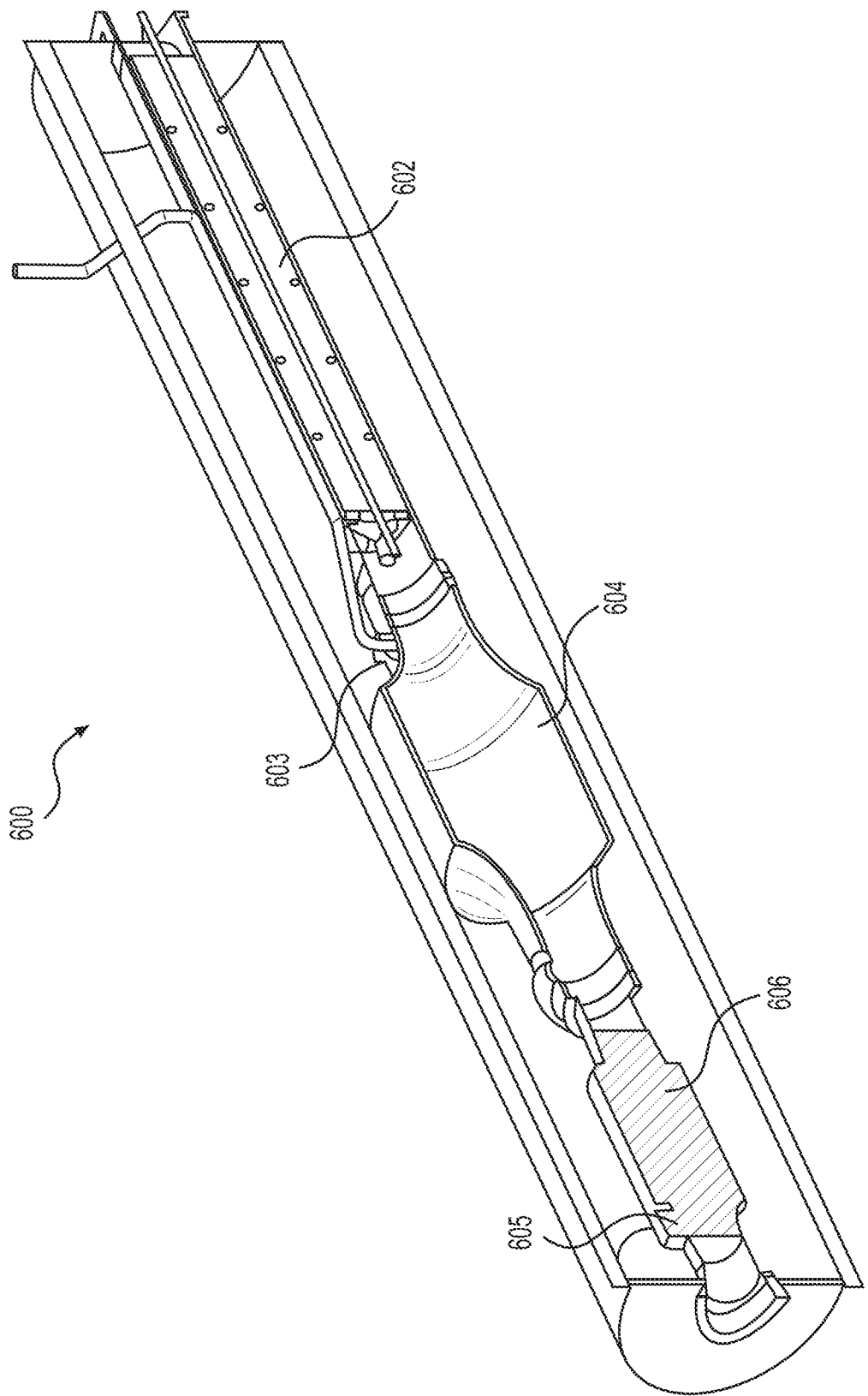
Figure 8:
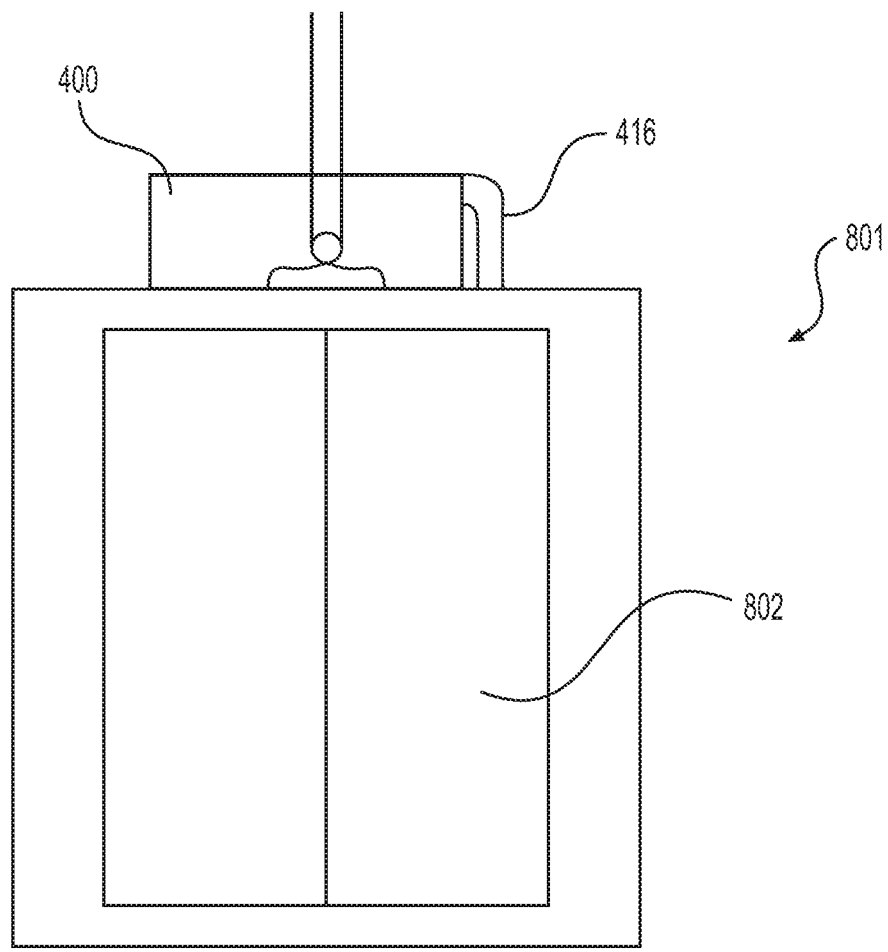

FIG. 6 shows a diagrammatic representation of another thermocatalytic converter 600 according to exemplary disclosed embodiments. FIG. 7 provides a cut-away perspective view of thermocatalytic converter 600. As shown, thermocatalytic converter 600 may include a heater 602, a first catalytic core 604, and a second catalytic core 606. A first temperature sensor 603 and a second temperature sensor 605 (as shown in FIG. 7) may be provided to monitor temperatures within zones of the thermocatalytic converter 600. Using the temperature information from these sensors may enable control of heater 602 in order to provide an air flow exhibiting a desired temperature profile.

Thermocatalytic converter 406 or 600 may include one or more mesh filters for capturing soot, ash, or other particles having a size generally greater than 100 microns. Particles of this kind are frequent in fire smoke in residences and workplaces, due to large quantities of plastic materials and polymers present in such environments. Such filters may prevent penetration into the system of particles that can contaminate the system and impact the activity of the gas purification stages. More specifically, converter 406 or 600 may have a 100 micron net fitted at an entrance to catch particles. The heaters in the cyclone will then complete the combustion of hydrocarbons that will adhere to the side walls before they reach the catalytic converter.

Also at this stage, input air pumped into the system will be heated (e.g., to about 300 degrees Celsius and will pass through catalytic converter 406 or 600, which will decompose gases therein.

The gases neutralized in this stage and the decomposition products thereof may include:

1) Oxidation of carbon monoxide and carbon dioxide:

$$2CO + O_2 \rightarrow 2CO_2$$

2) Reduction of the nitrogen oxide to nitrogen and oxygen:

$$2NO_x \rightarrow xN_2 + xO_2$$

3) Oxidation of the hydrocarbons to carbon dioxide and water:

$$C_xH_y + (x+y/4)O_2 \rightarrow xCO_2 + (y/2)H_2O$$

The oxygen released in the NOx reduction may participate in processes for oxidation of CO and hydrocarbons.

The catalytic conversion may be carried out by a ceramic catalytic converter. Converters of this type are made of a ceramic layer that has a honeycomb-like microscopic structure, designed to increase its surface area, covered by a metallic oxide (such as aluminum oxide, titanium oxide or silicon oxide). In some cases, these coarse surfaces may be covered with a reducing catalyst (such as rhodium), an oxidizing catalyst (palladium) and/or a two-purpose catalyst (platinum).

The thermo-catalytic unit will reduce the concentration of the aforementioned gases by an order of magnitude. As the efficiency of the catalytic converter becomes significant at a temperature higher than 230 degrees Celsius and reaches a peak at a temperature of 300 degrees Celsius, the system may heat the air entering the catalytic converter to a target of about 300 degrees Celsius. This temperature may also offer the benefit of destroying biological agents. The thermocatalytic unit may reduce a level of CO received in the input air flow from 20,000 ppm to less than 100 ppm.

The air entering the thermo-catalytic unit may be whirled and heated to 300 degrees C. by a double electrical heater, which may guarantee functionality even one of the heaters fails. The shown temperature sensors (FIG. 7), which may include thermocouples, may measure the temperature of the air entering the converter and can be used to control activation of the heaters, to ensure a desired operating temperature and to prevent unnecessary waste of energy by the heaters. Because the ignition temperature of soot is between 500° C. and 600° C., soot may be oxidized in the catalytic converter by using the heaters to provide an environment in this temperature range. It should be noted alternative configurations may be provided in which soot is filtered (e.g., using dry or wet filtering) rather than burned. Such configurations may offer a benefit of avoiding a need for cooling at later stages.

The passage through the catalytic converter 406 or 600 may cause the oxidation of CO and of hydrocarbons and the reduction of $NO_x$ and will produce nitrogen ($N_2$), water ($H_2O$), carbon dioxide ($CO_2$) and oxygen, which may participate in the oxidation of CO and hydrocarbons. These products will be released from the thermo-catalytic cyclone and may be transferred to the next stage of the purification process.

Initial stage converter 408 may provide the next stage of treatment in air treatment system 400. At this stage, fine-grained particles smaller than 20 microns may be removed from the air that underwent oxidation/reduction in the catalytic converter. This stage may also include an air treatment solution similar to the one described above with respect to air treatment unit 100. In some cases, a pump and flow equipment may be provided in order to transfer at least some air treatment solution from air treatment unit 100 to initial stage converter 408. At this stage, CO and other oxides, such as sulfur oxide, may be neutralized through reaction with the air treatment solution.

Another process that takes place at this stage is the initial cooling of the air to a temperature of approximately 100° C. The cooling of the air in this compartment may be caused by a water evaporation process. In this process, hot air arriving from the thermo-catalytic cyclone may be percolated through an air treatment solution, which may cause evaporation of water carried by the gas bubbles percolating through the air treatment solution. The high latent heat of evaporation (2,265 kJ/kg) causes cooling of the air within the bubbles. Additionally, cooling may occur through heat exchange with the water of the air treatment solution present in this stage. The specific heat of water is higher than that of air (approximately 4.2 kJ/kg K as compared to approximately 1 kJ/kg K), and therefore, "in exchange" for the temperature increase of 1 kg of solvent (water) by 1 degree, 600 liters of air (approx.) will cool by about 4 degrees. This unit may also remove at least some soot from the air flow.

Because of evaporation, the fluid level in Initial stage converter 408 may drop during operation. In order to maintain desired performance, a float sensor may be installed to report to the system controller the level of the solution in the compartment. When this level decreases under the established limit, the system controller will activate a pump that will transfer solution from the air treatment unit 100 to the initial stage converter 408.

Air exiting from the initial stage converter 408 may be provided to air treatment unit 100, which may operate as described above. Air treatment unit 100 may reduce an amount of one or more gaseous species from the air flow and may also provide cooling of the air flow.

It should be noted that air treatment unit 100 also contributes to cooling of the air flow. For example, as in initial stage converter 408, gas percolating through the aqueous air treatment solution of air treatment unit 100 may cool due to the evaporation of water and heat exchange with water. This cooling may cool air entering air treatment unit 100 such that air that enters at a temperature of 100 degrees C. may exit air treatment unit with a temperature less than 40 degrees C.

Due to high throughput through air treatment unit 100 (e.g., 300 to 600 liters of air per minute), the flow of the bubbles may be turbulent and may cause a strong mixing of the solution, which will ensure uniformity of the concentration of the reagents throughout the reactor.

Air treatment unit 100 may contribute to the neutralization of various chemical species through the following reactions:

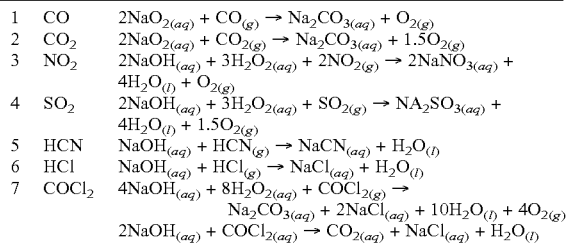

| 1 | CO | $2NaO_{2(aq)} + CO_{(g)} \rightarrow Na_2CO_{3(aq)} + O_{2(g)}$ |
| --- | --- | --- |
| 2 | $CO_2$ | $2NaO_{2(aq)} + CO_{2(g)} \rightarrow Na_2CO_{3(aq)} + 1.5O_{2(g)}$ |
| 3 | $NO_2$ | $2NaOH_{(aq)} + 3H_2O_{2(aq)} + 2NO_{2(g)} \rightarrow 2NaNO_{3(aq)} + 4H_2O_{(l)} + O_{2(g)}$ |
| 4 | $SO_2$ | $2NaOH_{(aq)} + 3H_2O_{2(aq)} + SO_{2(g)} \rightarrow NA_2SO_{3(aq)} + 4H_2O_{(l)} + 1.5O_{2(g)}$ |
| 5 | HCN | $NaOH_{(aq)} + HCN_{(g)} \rightarrow NaCN_{(aq)} + H_2O_{(l)}$ |
| 6 | HCl | $NaOH_{(aq)} + HCl_{(g)} \rightarrow NaCl_{(aq)} + H_2O_{(l)}$ |
| 7 | $COCl_2$ | $4NaOH_{(aq)} + 8H_2O_{2(aq)} + COCl_{2(g)} \rightarrow Na_2CO_{3(aq)} + 2NaCl_{(aq)} + 10H_2O_{(l)} + 4O_{2(g)}$ $2NaOH_{(aq)} + COCl_{2(aq)} \rightarrow CO_{2(aq)} + NaCl_{(aq)} + H_2O_{(l)}$ |

Treated air provided at the outlet of air treatment unit 100 may flow through one or more filters 410. Filters 410 may include any suitable type of filter. In some cases, filters 410 may include filters (such as CBRN filters) designed for removal of certain chemical or biological agents.

At this stage, the air may be pumped through an active carbon filter that meets the requirements of applicable government standards. A supplement may be added to adsorb $SO_2$ and humidity. This stage will represent a third backup layer for the mechanisms of neutralization of combustion products and CWM agents. The air may be drawn from the active carbon filter by two electrical pumps 412 with a flow rate of 600 liters of air per minute (or other appropriate rate), connected in series. In normal operation of the system, the pumps may be operated alternately in order to permit one of them to cool down while the other is working. Moreover, it may be possible to operate both pumps simultaneously to obtain a flow rate of more than 1000 liters of air per minute in order to rapidly build elevated air pressure in the space protected by the system.

Final cooling stage 414 may be provided to further cool air passing through air treatment system 400. Cooling stage 414 may include an aqueous heat exchange fluid. In some cases, cooling stage 414 relies upon substantially pure water to cool the air flow before passing the air flow to outlet 416. Cooling stage 414, along with cooling that may be provided by one or more of the other treatment modules of air treatment system 400, may ensure that the air exiting final outlet 416 is comfortable for breathing (e.g., below about 40 degree Celsius).

Air treatment system 400 may also include an air drying stage (not shown). At this stage, the air may be introduced into a cyclone where rapid rotary flow may cause tiny droplets of solution, which have a higher specific weight than the air in which they are carried, to stick to the walls of the cyclone and condense there. The solution collected at the bottom of the cyclone may be retrieved and pumped back to the air treatment system 100 (e.g., through a sedimentation container).

With the configurations described above, air treatment system 400 may convert an input flow of air including one or more contaminants and/or having a temperature up to 300 degrees C. into a supply of breathable, oxygen-enriched air. For example, air treatment system 400 may reduce the temperature of input air from up to 300 degrees C. to less than 40 degrees C.; reduce carbon dioxide from 100,000 ppm to less than 5,000 ppm; reduce carbon monoxide from 20,000 ppm to less than 50 ppm; reduce $NO_x$ from 20 ppm to less than 0.25 ppm; reduce HCN from 50 ppm to less than 10 ppm; reduce $COCl_2$ from 20 ppm to less than 0.2 ppm; reduce HCl from 50 ppm to less than 5 ppm; reduce $SO_2$ from 200 ppm to less than 5 ppm; and increase oxygen content from 14% to 21%.

Air treatment system 400, including air treatment unit 100, may be used with any environment where there may be a need to treat at least one aspect of air in the environment (e.g., reduction in a level of particulates, reduction in an amount of at least one gaseous constituent of the air, reduction or removal of one or more biological or chemical agents, etc.). For example, as shown in FIG. 8, air treatment system 400 may be incorporated with an elevator assembly 801. Such an installation may enable treatment of air contaminated by fire and may supply the treated air to a cabin 802 of the elevator. For example, as shown in FIG. 8, treated air supplied by air treatment system 400 may be provided to the elevator cabin 802 via air outlet 416. In view of the flow rates offered by air treatment system 400 of at least 300 liters per minute and up to about 600 liters per minute, air treatment system 400 may be capable of creating an overpressure in elevator cabin 802. In some embodiments, the overpressure in cabin 802 created by air treatment system 400 may be at least 0.8 millibars. Such an overpressure may reduce or eliminate contamination of air within the cabin 802 (e.g., caused by an influx of smoke, CO, etc. due to fire in an environment of the elevator) by causing a positive flow of air out of elevator cabin 802. The system shown in FIG. 8 may provide a supply of breathable air to cabin 802 at a rate of 300 to 600 liters/min, at a temperature less than 40 degrees Celsius, for a period of at least six hours.

Air treatment units similar to those described above may be configured for inclusion in any system where there is a need to treat or change at least one characteristic of a volume of air. For example, FIG. 9 provides a diagrammatic representation of a personal breather system 900 that includes an air treatment unit 901. In such embodiments, air treatment unit 901 may be configured to remove breathing byproducts, such as carbon dioxide, from a flow of air. Through operation of the wet or semi-wet scrubbing techniques similar to those described above, carbon dioxide may be removed from air exhaled by the user and a flow of air enriched with oxygen may be provided to the user to breathe. More specifically, with reference to FIG. 9, personal breather system 900 may include a housing 902 that may contain one or more components of air treatment unit 901 and any other suitable components for treating a flow of air.

In the embodiment shown, air treatment unit 901 may include an oxidizing agent reservoir 910, an oxidizing agent pump 914, and one or more reaction reservoirs 916. As shown, air treatment unit 901 includes three reaction reservoirs 916*a*, 916*b*, and 916*c* each configured in a canister form. Air treatment unit 901 may include a controller (not shown) for controlling a supply of oxidizing agent (e.g., hydrogen peroxide, or any oxidizing agent described above, etc.) to the reaction reservoirs 916, which may include an alkali hydroxide, such as any of the alkali hydroxides described above. Air treatment unit 901 may also include an air dispersing element 918 configured to produce microbubbles. As shown in FIG. 9, air dispersing element 918 may include three sub-elements 918*a*, 918*b*, and 918*c*, each disposed in a respective reaction reservoir. Air dispersing element 918 may have any of the characteristics of air dispersing element 406 described above and may produce microbubbles having any of the characteristics described above relative to microbubbles 408.

During operation, a user may engage with a mouthpiece 906 and begin breathing. A supply of oxidizing agent may be provided from reservoir 910 to reaction reservoirs 916. A controller (not shown) included with air treatment unit 901 may sense the presence of exhaled air in mouthpiece 906 or hose 908 and may respond by turning on pump 914 to supply oxidizing agent to reaction reservoirs 916. Further, the controller may determine an amount of a constituent in the exhaled air (e.g., carbon dioxide) based on the output of an air quality sensor (not shown) in mouthpiece 906 or hose 908 (or other suitable position) and use that information as a trigger to add more oxidizing agent to reaction reservoirs 916 (e.g., if a carbon dioxide level is too high), or to halt a flow of oxidizing agent (e.g., if a carbon dioxide level is below a predetermined threshold). The system may convert exhaled air that contains a high concentration of carbon dioxide (4%) and low concentration (16%) of oxygen to safe, breathable air that contains a high concentration of oxygen (20%+) and low concentration of carbon dioxide (0.038% or less).

The oxidizing agent supplied to the reaction reservoirs 916 may mix with alkali hydroxide present in reaction reservoirs 916 to form an aqueous air treatment solution including superoxide anions (formed through reaction of the oxidizing agent with the alkali hydroxide) capable of reaction with carbon dioxide. An exhaled air pump 912 may pull air to be treated (e.g., air rich in exhaled carbon dioxide) from mouthpiece 906, through an exhaled air hose 908 (or other type of conduit) and provide the air to be treated to reaction reservoirs 916. For example, the air to be treated may be converted to a plurality of microbubbles by air dispersion elements 918, which, as shown, may have a cylindrical configuration to emit microbubbles into the cylindrical reaction reservoirs. The microbubbles may be produced in the aqueous air treatment solution present within the reaction reservoirs 916. The shape of the reaction reservoirs and/or the configuration of the plurality of holes associated with the air dispersing elements 918 may cause the formed microbubbles to take a non-straight path through the aqueous air treatment solution. In some cases, the microbubbles may swirl within the air treatment solution.

Gases in the produced microbubbles may react with the superoxide anions of the aqueous air treatment solution and, as a result, an amount of a gas, such as carbon dioxide, may be reduced as the air is treated. Treated air can be collected at the top of reaction reservoirs 916 and may be passed through a treated air intake hose 904 (or other type of air conduit) to mouthpiece 906. The treated air may be breathed directly by the user of personal breather system 900. In view of the efficiencies provided by the wet or semi-wet scrubbing techniques described and the ability to mix the active reagents only when needed and only in amounts needed, personal breather system 900 may be capable of significantly reducing levels of carbon dioxide within exhaled air. Further, using the air dispersion techniques employing air dispersing element configured to produce microbubbles, personal breather system 900 may be capable of maintain flow rates in a range of about five to 50 liters per minute.

In some embodiments, one or more additional mouthpieces (not shown) may be provided to enable multiple users to effectively share air produced by personal breather system 900. Additionally or alternatively, personal breather system may include one or more masks (not shown) to act as a conduit for providing treated air to users of the system while covering at least a portion of the users' faces. Supplying air to multiple users (including, e.g., a firefighter and one or more fire victims), may be possible due to the flow rates of ten to 100 liters per minute that can be provided by personal breather system 900. Moreover, because the superoxide active material may be generated on an as-needed basis, the operational life of the air treatment unit may depend on the severity of conditions encountered. For example, during normal breathing of a single user, the system may provide four hours or more of oxygen-enriched air from a single pack weighing less than five kg. Moreover, because the system contains no reservoir of oxygen, it may be safer for use by firefighters in fire conditions than oxygen tanks.

Air treatment unit 901 may include one or more flow limiters 920 configured to reduce or eliminate a flow of aqueous air treatment solution from reaction reservoirs 916 to mouthpiece 906 (or any other mouthpiece or mask associated with air treatment unit 901). Such a flow limiter may be disposed, for example, at an outlet of reaction reservoirs 916, within hose 904, or at any other suitable location. Any type of flow limiter may be used. In some embodiments, flow limiter 920 may include one or more one-directional valves, moisture blocking membranes, etc.

The air treatment units and systems described above may be used to perform air treatment methods. In some embodiments, the units systems may be used to perform a method including flowing air to be treated into an air inlet of a reaction reservoir, wherein the reaction reservoir includes an air treatment solution including a mixture of hydrogen peroxide and alkali hydroxide; converting at least a portion of the flow of air to be treated into a plurality of microbubbles using an air dispersing element; introducing the microbubbles into the air treatment solution, such that an amount of one or more target gas species contained within the plurality of microbubbles is reduced through reaction with one or more constituents of the air treatment solution; and outputting treated air from the reaction reservoir.

In some embodiments, the methods of the presently disclosed embodiments may further include automatically determining, from an output of an air quality sensor, a level of at least one constituent in an air flow; automatically determining whether the level of the at least one constituent exceeds a predetermined threshold; and after determining that the level of the at least one constituent exceeds the predetermined threshold, initiating transfer into the reaction reservoir of a supply of oxidizing agent via a first reagent inlet.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. An air treatment unit, comprising:
an air inlet to receive a flow of input air for treatment;
a reaction reservoir configured to hold an aqueous air treatment solution;
an air dispersing element flow connected with the air inlet, wherein the air dispersing element is configured to convert at least a portion of the flow of input air into a plurality of microbubbles for introduction into the aqueous air treatment solution, such that an amount of one or more target gas species contained within the plurality of microbubbles is reduced through reaction with the aqueous air treatment solution;

a pH sensor configured to generate an output indicative of a pH level of a solution in the reaction reservoir; and an air outlet configured to output treated air from the reaction reservoir.

2. The air treatment unit of claim 1, wherein the air dispersing element includes a plurality of holes configured to emit the microbubbles.

3. The air treatment unit of claim 2, wherein the plurality of holes have an average diameter of between 0.5 microns and 500 microns.

4. The air treatment unit of claim 2, wherein the plurality holes have an average diameter of between 10 microns and 100 microns.

5. The air treatment unit of claim 2, wherein the plurality of holes are separated from one another by an average distance that is between two times and 30 times an average diameter of the plurality of holes.

6. The air treatment unit of claim 2, wherein the plurality of holes are separated from one another by an average distance that is between six times and eight times an average diameter of the plurality of holes.

7. The air treatment unit of claim 2, wherein the plurality of holes are distributed across at least a portion of the air dispersing element with a distribution density of between one and 100 holes per square centimeter.

8. The air treatment unit of claim 2, wherein the plurality of holes are distributed across at least a portion of the air dispersing element with a distribution density of between three and seven holes per square centimeter.

9. The air treatment unit of claim 1, wherein the air dispersing element includes a stainless steel foil.

10. The air treatment unit of claim 9, wherein the stainless steel foil is at least partially coated with nickel.

11. The air treatment unit of claim 1, wherein the air dispersing element is configured to generate microbubbles having an average diameter of less than 1 millimeter.

12. The air treatment unit of claim 1, wherein the air dispersing element is configured to generate microbubbles having an average diameter of between 1 and 100 microns.

13. The air treatment unit of claim 1, wherein the air dispersing element is configured to generate microbubbles having an average diameter of between 5 and 50 microns.

14. The air treatment unit of claim 1, wherein the air dispersing element is configured to generate microbubbles of which at least 80% have an average diameter of between 10-70 microns.

15. The air treatment unit of claim 1, wherein the microbubbles generated by the air dispersing element have a mean free path in the air treatment solution that ranges from 0.01 cm to 25 cm.

16. The air treatment unit of claim 1, wherein the at least 80% of the microbubbles generated by the air dispersing element have a mean free path of at least 1 mm.

17. The air treatment unit of claim 1, wherein the aqueous air treatment solution includes an oxidizing agent and at least one alkali hydroxide.

18. The air treatment unit of claim 17, wherein the oxidizing agent includes at least one of hydrogen peroxide, permanganate, persulfate, or combinations thereof.

19. The air treatment unit of claim 17, wherein the air treatment solution has an oxidizing agent to alkali hydroxide ratio of at least 1:1 and up to 1.6:1.

20. The air treatment unit of claim 17, wherein the air treatment solution has an oxidizing agent to alkali hydroxide ratio of at least 1:1 and up to 4:1.

21. The air treatment unit of claim 17, wherein the alkali hydroxide includes one or more of sodium hydroxide, calcium hydroxide, potassium hydroxide, lithium hydroxide, trisodium phosphate, tripotassium phosphate, triethanolamine, or combinations thereof.

22. The air treatment unit of claim 1, wherein the aqueous air treatment solution includes hydrogen peroxide having a molarity between SM and SOM.

23. The air treatment unit of claim 1, wherein the aqueous air treatment solution includes alkali hydroxide having a molarity of between 3M and 30M.

24. The air treatment unit of claim 1, wherein the aqueous air treatment solution has a pH of between 10 and 12.5.

25. The air treatment unit of claim 1, wherein the aqueous air treatment solution includes a superoxide anion formed by reaction of hydrogen peroxide with at least one alkali hydroxide.

26. The air treatment unit of claim 1, wherein the aqueous air treatment further includes a phase transfer catalyst.

27. The air treatment unit of claim 26, wherein the phase transfer catalyst includes an ammonium salt.

28. The air treatment unit of claim 1, wherein the reaction reservoir includes a first reagent inlet configured to allow into the reaction reservoir a supply of hydrogen peroxide, and wherein the reaction reservoir includes a second reagent inlet configured to allow into the reaction reservoir a supply of alkali hydroxide.

29. The air treatment unit of claim 28, wherein the air treatment unit further includes:

an air quality sensor configured to generate an output indicative of a level of at least one constituent in air treatable by the air treatment unit; and at least one controller programmed to:

monitor the output of the air quality sensor to determine a level of the at least one constituent;

threshold; and determine whether a level of the at least one constituent exceeds a predetermined after a determination that the level of the at least one constituent exceeds the predetermined threshold, initiate transfer into the reaction reservoir of the supply of hydrogen peroxide via the first reagent inlet, initiate transfer into the reaction reservoir of the supply of alkali hydroxide via the second reagent inlet, and cause at least some of the air treatable by the air treatment unit to enter the air inlet.

30. The air treatment unit of claim 29, wherein the air quality sensor is located remotely with respect to the air treatment unit.

31. The air treatment unit of claim 28, wherein the air treatment unit further includes:
an air quality sensor configured to generate an output indicative of a level of at least one constituent in treated air output by the air treatment unit; and
at least one controller programmed to:
monitor the output of the air quality sensor to determine a level associated with the at least one constituent;
determine whether a level of the at least one constituent exceeds a predetermined threshold; and
after a determination that the level of the at least one constituent exceeds the predetermined threshold, initiate transfer into the reaction reservoir of a portion of the supply of hydrogen peroxide via the first reagent inlet.

32. The air treatment unit of claim 31, further comprising initiation of transfer into the reaction reservoir of a portion of the supply of alkali hydroxide via the second reagent inlet after a determination that the level of the at least one constituent exceeds the predetermined threshold.

33. The air treatment unit of claim 31, wherein the air quality sensor is positioned to interact with air in the air outlet.

34. The air treatment unit of claim 28, wherein the air treatment unit further includes:
at least one controller programmed to:
monitor the output of the pH sensor to determine a pH level of the solution in the reaction reservoir;
determine how the pH level of the solution in the reaction reservoir compares to at least one of a target pH level or a target pH range; and
after a determination that the pH level of the solution in the reaction reservoir differs from the target pH level by more than a threshold difference or falls outside of the target pH range, initiate transfer into the reaction reservoir of at least one of the supply of hydrogen peroxide via the first reagent inlet or the supply of alkali hydroxide via the second reagent inlet.

35. The air treatment unit of claim 28, wherein the air treatment unit further includes:
a fluid level sensor configured to generate an output indicative of a fluid level of a solution in the reaction reservoir; and
at least one controller programmed to:
monitor the output of the fluid level sensor;
after a determination that a fluid level in the reaction reservoir has fallen below a target fluid level, initiate transfer into the reaction reservoir of at least one of the supply of hydrogen peroxide via the first reagent inlet, the supply of alkali hydroxide via the second reagent inlet, or a supply of water through a water inlet.

36. The air treatment unit of claim 1, further including one or more pumps for drawing air into the air inlet or for causing air to flow from the air outlet.

37. The air treatment unit of claim 1, further including a condenser unit downstream of the air outlet and configured to collect aqueous air treatment solution carried by treated air passing out of the air outlet.

38. The air treatment unit of claim 1, further including a thermocatalytic unit upstream from the air inlet, wherein the thermocatalytic unit includes:
a heater configured to heat air passing therethrough to a temperature in the range of 80 degrees Celsius to 500 degrees Celsius; and
a catalytic converter configured to receive the heated air.

39. The air treatment unit of claim 38, wherein the heater is powered by at least one of electric power or fuel gas combustion.

40. The air treatment unit of claim 1, further comprising one or more particulate filters.

41. The air treatment unit of claim 1, wherein the air treatment unit is configured to reduce an amount of carbon monoxide from the input air by at least a factor of 100.

42. The air treatment unit of claim 1, wherein the air treatment unit is configured to reduce a temperature of the input air by at least a factor of two.

43. The air treatment unit of claim 1, wherein the air treatment unit is configured to process the input air at a flow rate of between 300 liters per minute to 600 liters per minute.

44. An elevator fitted with the air treatment unit of claim 1, wherein the elevator includes a cabin, and treated air passing from the air outlet flows toward the cabin.

45. The elevator of claim 44, wherein the air treatment unit is configured to provide an overpressure in the cabin of at least 0.8 mbar.

46. The elevator of claim 44, wherein treated air provided to the cabin has a temperature of no more than 40 degrees Celsius.

47. A personal breathing apparatus including the air treatment unit of claim 1.

48. The personal breathing apparatus of claim 47, wherein the air treatment unit is configured to process the input air at a flow rate of least 10 liters per minute to 100 liters per minute.

49. The personal breathing apparatus of claim 47, further including a breathing interface flow connected to the air outlet and configured to provide at least a portion of the treated air to a user of the personal breathing apparatus.

50. The personal breathing apparatus of claim 49, wherein the breathing interface includes at least one of a mouthpiece or a mask.

51. The personal breathing apparatus of claim 47, further including two or more breathing interfaces flow connected to the air outlet and configured to provide at least a portion of the treated air to two or more users of the personal breathing apparatus.

52. The personal breathing apparatus of claim 49, further including a flow limiter to limit flow of the aqueous air treatment solution into the breathing interface.

53. The personal breathing apparatus of claim 47, further including a flow path configured to receive air exhaled by a user of the personal breathing apparatus and provide the exhaled air to the air inlet of the air treatment unit.

54. A method of treating air with an air treatment unit, the method comprising:
flowing air to be treated into an air inlet of a reaction reservoir, wherein the reaction reservoir includes an air treatment solution including a mixture of an oxidizing agent and alkali hydroxide;
converting at least a portion of the flow of air to be treated into a plurality of microbubbles using an air dispersing element;
introducing the microbubbles into the air treatment solution, such that an amount of one or more target gas species contained within the plurality of microbubbles is reduced through reaction with one or more constituents of the air treatment solution;
generating, by a sensor, an output indicative of a pH level of a solution in the reaction reservoir; and
outputting treated air from the reaction reservoir.

55. The method of claim 54, further comprising:
automatically determining, from an output of an air quality sensor, a level of at least one constituent in a volume of air;

automatically determining whether the level of the at least one constituent exceeds a predetermined threshold; and after determining that the level of the at least one constituent exceeds the predetermined threshold, initiating transfer into the reaction reservoir of a supply of the oxidizing agent via a first reagent inlet.

56. The method of claim 55, further including initiating transfer into the reaction reservoir of a supply of the alkali hydroxide via a second reagent inlet.

57. The method of claim 55, wherein the oxidizing agent includes at least one of hydrogen peroxide, permanganate, persulfate, or combinations thereof.

58. The method of claim 55, wherein the air quality sensor is positioned downstream of the reaction reservoir.

59. The method of claim 55, wherein the air quality sensor is positioned upstream of the air inlet of the reaction reservoir.

\* \* \* \* \*